US00PP23119P2

(12) United States Plant Patent
van den Bosch

(10) Patent No.: US PP23,119 P2
(45) Date of Patent: Oct. 16, 2012

(54) *HYPERICUM* PLANT NAMED 'BOSAFIR'

(50) Latin Name: *Hypericum androsaemum*
Varietal Denomination: Bosafir

(76) Inventor: Bernard Rene van den Bosch, Rijnsburg (NL)

( * ) Notice: Subject to any disclaimer, the term of this patent is extended or adjusted under 35 U.S.C. 154(b) by 25 days.

(21) Appl. No.: 13/065,683

(22) Filed: Mar. 28, 2011

(51) Int. Cl.
*A01H 5/00* (2006.01)

(52) U.S. Cl. ..... Plt./442

(58) Field of Classification Search ..... Plt./442
See application file for complete search history.

(56) References Cited

OTHER PUBLICATIONS

UPOV-Pluto Plant Variety Database, 2011/06; cultivar name 'Bosafir' (1 page total).*

* cited by examiner

*Primary Examiner* — Susan McCormick Ewoldt
(74) *Attorney, Agent, or Firm* — Penny J. Aguirre

(57) ABSTRACT

A new cultivar of *Hypericum androsaemum*, 'Bosafir', characterized by its unique berries that are large in size, oval to oblong in shape, and bright red in color.

2 Drawing Sheets

Botanical classification: *Hypericum androsaemum.*
Variety denomination: 'Bosafir'.

BACKGROUND OF THE INVENTION

The present invention relates to a new and distinct cultivar of *Hypericum androsaemum* and will be referred to hereafter by its cultivar name, 'Bosafir'. 'Bosafir' is a shrub grown for use as a landscape plant and for use as stem cutting with flowers and fruits.

'Bosafir' was selected in the Inventor's greenhouse in Rijnsburg, The Netherlands in August 2002 as a single unique plant from amongst the seedlings derived from a cross made in June 2001 between an unnamed plant from the Inventor's breeding program, code no. Nr 16, as the female parent and an unnamed plant from the Inventor's breeding program, code no. Nr 22, as the male parent.

Asexual reproduction of the new cultivar was first accomplished by stem cuttings in Rijnsburg, The Netherlands in June of 2002. The characteristics of this cultivar have been determined to be stable and are reproduced true to type in successive generations.

SUMMARY OF THE INVENTION

The following traits have been repeatedly observed and represent the characteristics of the new cultivar as grown outdoors in a test plot in Rijnsburg, The Netherlands. These attributes in combination distinguish 'Bosafir' as a unique cultivar of *Hypericum.*

1. 'Bosafir' exhibits berries that are large in size.
2. 'Bosafir' exhibits berries that are bright red in color.
3. 'Bosafir' exhibits berries that are oval to oblong in shape.

'Bosafir' can be compared to its parent plants. The female parent, Nr 16, differs from 'Bosafir' in having berries that are flatter in shape and dull brown in color. The male parent, Nr 22, differs from 'Bosafir' in having berries that are smaller in size. 'Bosafir' can be most closely compared to the cultivars 'Bosapin' (U.S. Plant Pat. No. 10,993) and 'Bosaja' (U.S. Plant Pat. No. 14,182). 'Bosapin' differs from 'Bosafir' in having berries that are smaller in size and less red in color. 'Bosaja' differs from 'Bosafir' in having berries that are smaller in size and green in color.

BRIEF DESCRIPTION OF THE DRAWING

The accompanying colored photographs were taken in July and illustrate the overall appearance and distinct characteristics of a two year-old plant the new *Hypericum* as grown in a field plot in Rijnsburg, The Netherlands.

The photograph in FIG. 1 is a side view of 'Bosafir' with both flowers and fruit.

Figure 1:
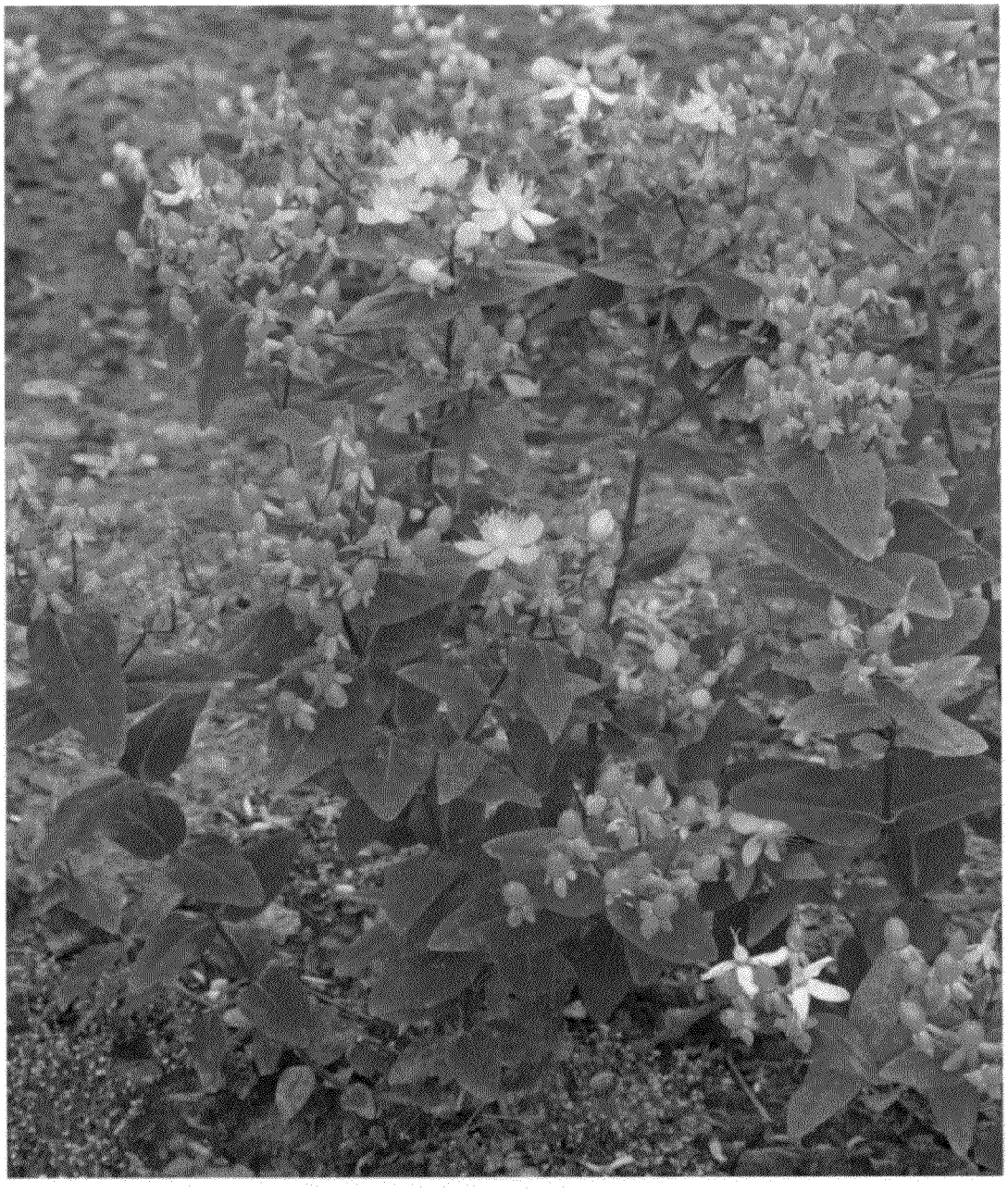
Figure 2:
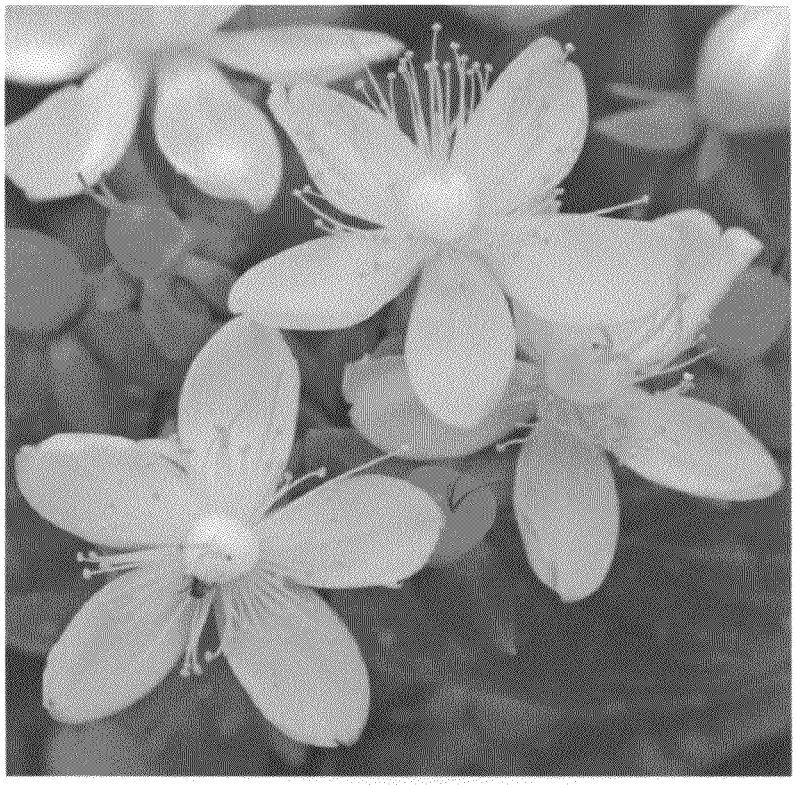

The photograph in FIG. 2 provides a close-up view of the flowers of 'Bosafir'.

Figure 3:
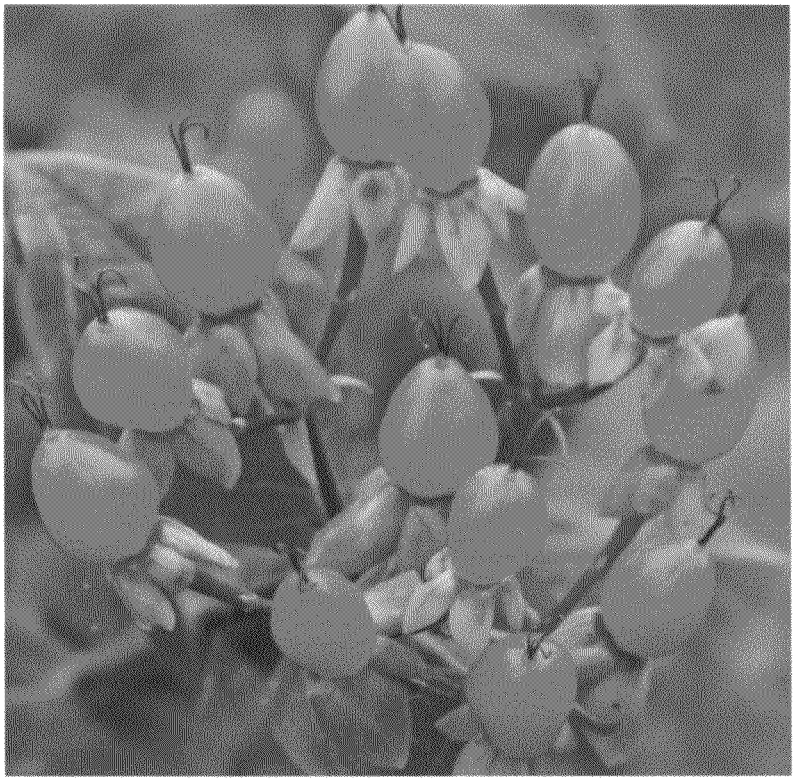

The photograph in FIG. 3 provides a close-up view of the berries of 'Bosafir'. The colors in the photograph may differ slightly from the color values cited in the detailed botanical description, which accurately describe the colors of the new *Hypericum.*

DETAILED BOTANICAL DESCRIPTION

The following is a detailed description of two year-old plants of the new cultivar as field grown in Rijnsburg, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms continuously from July to into September in Rijnsburg, The Netherlands.

*Plant type.*—Perennial shrub.

*Plant habit.*—Broadly upright.

*Height and spread.*—Reaches about 64.4 cm in height and about 51.3 cm in width.

*Cold hardiness.*—U.S.D.A. Zone 5 to 9.

*Diseases and pests*.—No susceptibility or resistance to diseases or pests has been observed.

*Root description*.—Fibrous, freely branched.

Growth and propagation:

*Propagation*.—Terminal, softwood stem cuttings.

*Growth rate*.—Moderate.

Stem description:

*Shape*.—Round.

*Stem color*.—A color between 183A to 187C.

*Stem size*.—Average of 6 main stems; lateral branches; up to about 40.3 cm in length and 4 mm in width.

*Stem surface*.—Smooth, very slightly glossy.

*Internode length*.—An average of 5.3 cm.

*Branching*.—Freely branched with main shoots growing from the base.

Foliage description:

*Leaf shape*.—Ovate.

*Leaf division*.—Single.

*Leaf base*.—Truncate.

*Leaf apex*.—Obtuse.

*Leaf fragrance*.—None.

*Leaf venation*.—Pinnate, upper side; 145A in color, lower side; 145C in color.

*Leaf margins*.—Entire.

*Leaf arrangement*.—Opposite.

*Leaf attachment*.—Sessile.

*Leaf surface*.—Smooth and very slightly rugose on upper and lower surface.

*Leaf size*.—Up to about 6.5 cm in length, up to 3.7 cm in width.

*Leaf color*.—Young upper surface; 144A, mature upper surface; N137C, young lower surface; a color between 144B and 144C, mature lower surface; 138B.

Inflorescence description:

*Inflorescence type*.—Cyme of approximately 15 flowers.

*Inflorescence size*.—About 8.4 cm in length and 11 cm in width.

*Lastingness of inflorescence*.—Flowers last a few days, berries last about 30 days and about 2 weeks on a cut stem.

*Flower buds*.—Obovate in shape, up to 11 mm in length and 8 mm in width, 12B in color and 13A at the apex.

*Flower fragrance*.—None detected.

*Flower quantity*.—About 43 per branch, an average of 300 per plant.

*Flower type*.—Single.

*Flower shape*.—Rotate.

*Flower aspect*.—Upright.

*Flower size*.—Average of 3.1 cm in diameter and 2 cm in depth.

*Petals*.—5, obovate in shape, un-fused, slightly reflex, upper and lower surfaces are dull and shiny, entire margin, rounded to bluntly acute apex, about 1.8 cm in length and 0.9 cm in width, upper surface when opening; 13A, lower surface when opening; 12A, upper surface when fully opened; between 13A and 13B, lower surface when fully opened; between 12A and 12B, petal color fading to 14B on both surfaces.

*Calyx*.—Rotate in shape, about 1.8 cm in diameter and 5 mm in depth.

*Sepals*.—5, ovate in shape, smooth and dull surface, about 1.3 cm in length and 7 mm in width, entire margin, round apex, broadly cuneate base, young upper surface color; 144A, base tinged with 181A and 181B, mature upper surface color; 143A and suffused with 144A, base tinged 175A, young lower surface color; 146C, base tinged 180A, mature lower surface color; 144B, base slightly tinged with 182B.

*Peduncles*.—Moderately strong, about 3.3 cm in length, 1 mm in diameter, ranges from 178A to 178B in color, angle of main peduncle straight on top of lateral branch 0°, an average angle of secondary peduncles 50°.

*Pedicels*.—Moderately strong, about 1 cm in length, 1 mm in diameter, 177B with areas of 143B in color, angle of main pedicels straight on top of lateral branch 0°, an average angle of secondary pedicels 50°.

Reproductive organs:

*Gynoecium*.—3 pistils, about 8 mm in length, styles are 8B in color and about 7.5 mm in length, stigmas are club-shaped and 34B in color, ovary ranges from 8B to 8C in color.

*Androcoecium*.—An average of 75 stamens, filaments are 12A in color, about 1.5 cm in length, anthers are 25B in color, about 0.5 mm in length, dorsifixed, very small amount of pollen, too little to determine color.

*Fruit*.—51 per lateral branch, average of 300 per plant, smooth and glossy in texture, 25 days to fruit ripening, 30 days keeping quality, oval to oblong in shape, about 1.3 cm in length (excluding the three persistent dry pistil styles on top of the fruit), about 1 cm in diameter, 46B in color and becoming lighter towards the base 56D, 3 pistil styles are persistent on top of the fruit.

*Seed*.—More than 100 per fruit, about 0.8 mm in length, 0.5 mm in diameter, mature to N199A in color.

It is claimed:

1. A new and distinct cultivar of *Hypericum* plant named 'Bosafir' as herein illustrated and described.

* * * * *